United States Patent
Buehner et al.

(10) Patent No.: US 8,483,434 B2
(45) Date of Patent: Jul. 9, 2013

(54) TECHNIQUE FOR REGISTERING IMAGE DATA OF AN OBJECT

(75) Inventors: Ulrich Buehner, Denzlingen (DE); Lars Metz, Freiburg (DE); Amir Sarvestani, Freiburg (DE); Hans Schoepp, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 375 days.

(21) Appl. No.: 12/886,823

(22) Filed: Sep. 21, 2010

(65) Prior Publication Data

US 2011/0069867 A1    Mar. 24, 2011

(30) Foreign Application Priority Data

Sep. 21, 2009  (EP) .................................... 09011985

(51) Int. Cl.
*G06K 9/00* (2006.01)
*G06K 9/32* (2006.01)

(52) U.S. Cl.
USPC ........................ 382/103; 382/154; 382/294

(58) Field of Classification Search
USPC .............. 382/103, 128, 131, 154, 294; 378/4, 378/163–165; 600/424–426
See application file for complete search history.

(56) References Cited

U.S. PATENT DOCUMENTS

| | | | |
|---|---|---|---|
| 6,205,411 B1 * | 3/2001 | DiGioia et al. .................. | 703/11 |
| 6,226,548 B1 | 5/2001 | Foley et al. | |
| 6,527,443 B1 | 3/2003 | Vilsmeier et al. | |
| 6,738,656 B1 | 5/2004 | Ferre et al. | |
| 7,251,522 B2 | 7/2007 | Essenreiter et al. | |
| 2004/0082854 A1 | 4/2004 | Essenreiter et al. | |
| 2004/0127788 A1 | 7/2004 | Arata | |
| 2004/0171924 A1 * | 9/2004 | Mire et al. .................... | 600/407 |
| 2009/0234217 A1 * | 9/2009 | Mire et al. .................... | 600/407 |
| 2010/0046718 A1 * | 2/2010 | Weiser et al. ................. | 378/163 |

FOREIGN PATENT DOCUMENTS

| | | |
|---|---|---|
| EP | 1571581 A1 | 9/2005 |
| EP | 2 156 790 A1 | 2/2010 |

OTHER PUBLICATIONS

European Office Action dated Aug. 23, 2012, issued in corresponding European Patent Application No. 10 009 959.7, (4 pages).

* cited by examiner

*Primary Examiner* — Daniel Mariam
(74) *Attorney, Agent, or Firm* — Westerman, Hattori, Daniels & Adrian, LLP

(57) ABSTRACT

Three-dimensional image data generated for an object is representative of at least a portion of the object and of reference markings associated with the object. The reference markings have a known spatial relationship with a registration tracker tracked by a navigation system. Registration tracking data/object tracking data, each representative of at least one of a spatial location and a spatial orientation of the registration tracker/object tracker respectively, are provided. The object tracker has a fixed spatial relationship with the object. The relative position between the registration tracker and the object tracker is calculated from the registration tracking data and the object tracking data for a given point in time. Registered image data is generated representative of the location or the orientation of the object, taking into account the spatial relationship between the reference markings and the registration tracker, and the relative position between the registration tracker and the object tracker.

29 Claims, 12 Drawing Sheets

TECHNIQUE FOR REGISTERING IMAGE DATA OF AN OBJECT

TECHNICAL FIELD

The present disclosure generally relates to an image registration technique. In particular, a technique for registering image data of an object with at least one of a location and an orientation of the object is disclosed.

BACKGROUND

Registration of image data with the location or orientation of an imaged object is one of the biggest challenges for an image-assisted navigation procedure, for instance during a surgical operation. The precision of the entire navigation procedure, and thus the surgical result, strongly depend on the registration quality.

There are numerous registration procedures that typically require auxiliary devices or manual interaction of the surgeon. Common examples are paired-points registration by matching single points obtained from pre-operative image data manually or automatically with corresponding points on the patient, and surface registration procedures by matching a defined surface of the pre-operative image data with the corresponding surface of the patient.

Many registration procedures are based on so-called fiducials. Fiducials are reference markings that are attached to the anatomy of the patient before imaging and that also show up in the image data. Conventionally, the fiducials themselves form the transitional items which allow registration between the virtual data space and the physical world. The fiducials have known relative positions to a navigational patient tracker and are attached together with the tracker to the anatomy to be tracked. By knowing the fiducial positions with respect to the tracker, the patient anatomy can automatically be registered for navigation. Prior to registration, it is typically required that at any part that needs to be tracked, and where a tracker is attached, a set of points needs to be identified for matching purposes.

Another registration procedure is based on attaching dedicated trackers to the imaging device and recording their position in space relative to the navigation system. This procedure requires a special adaptation of the imaging device.

A manually performed registration procedure based on fiducials attached to the patient prior to pre-operative imaging is disclosed in U.S. Pat. No. 6,226,548 B1. An identification superstructure including a reference arc and a fiducial array is connected to an attaching device which is fixed to a body (bony) part of a patient. The fiducial array has the function of identifying the location of the superstructure and the body part during imaging (e.g., by a Computer Tomography (CT) scan or Magnetic Resonance Imaging (MRI)) and is detectable by a navigation system.

After the pre-operative scan, the identification superstructure is removed from the attaching device and placed back on the patient in the operating room. The fiducial array and, therefore, the location of the body part is registered in a surgical navigation system by manually pointing to the fiducials with a pointer device of the navigation system. Such manually performed registration procedures are in general time-consuming and imprecise.

Automatic registration procedures are also common particularly in combination with intra-operative imaging. An intra-operative imaging scenario based on a tracking of the imaging device is described in U.S. Pat. No. 7,251,522 B. Before the surgical operation, a calibrating procedure has to be performed in order to define a spatial relationship between a 3D imaging volume and the imaging device, with the calibration device being centered in the 3D imaging volume. The calibration device is removed after the calibration procedure. Then, image data of the patient body are scanned and both the patient and the imaging device are continuously tracked by the navigation system in order to establish a spatial relationship between the patient and the image data and to perform automatic registration.

A similar pre-calibrating processing is described in US 2004/0127788 A1. A scanner calibrator is used to pre-calibrate a scanner by determining a transformation for mapping points and coordinates in images taken by the scanner to the position of a scanner tracker. After the scanner calibrator is removed, a transformation for mapping images from the scanner taken during an interventional procedure to a patient tracker is determined based on the locations of the patient tracker and the scanner tracker. Thereby, the images are registered to the patient. Thus, this registration procedure requires a tracker attached to the imaging device. Further, an additional calibration process is necessary before starting a surgical operation.

It is known that image registering systems as known from U.S. Pat. No. 7,251,522 B and US 2004/0127788 A1 use trackers mounted on imaging devices, such as a CT scanner or a MRI device, are limited in their possibilities. Only the pre-calibrated imaging device can be used for a surgical operation, since otherwise, it is not possible to map image data. Moreover, the imaging device needs to be recalibrated when the imaging device or the tracker thereof has been moved.

In U.S. Pat. No. 6,527,443 B1 another technique for a navigation-assisted treatment of a body part is disclosed. The technique comprises providing a C-arm with a reference structure including a fiducial array and a tracker to be tracked by a navigation system. A two-dimensional (2D) X-ray image of both the body part of the patient and the reference structure is taken, and the location of the body part is determined from the X-ray image and the tracking data generated by the navigation system. The patient needs to be fixed during the operation, since no patient tracking takes place.

A further automatic registration procedure is disclosed in U.S. Pat. No. 6,738,656 B1. The automatic registration is performed by attaching an array of imaging phantoms or fiducials forming a reference unit to the patient prior to imaging. Then a tracker is attached to the reference unit in a fixed spatial relationship with respect to the array of fiducials. The automatic registration process locates the fiducials on the prerecorded scan images, and, based on the known spatial relationship between the fiducials and the tracker, automatically generates a transformation function.

The automatic registration procedures discussed above allow for registration of the imaged anatomy with a coordinate system of the navigation system, but need complicated adaptations, trackers to be attached to the imaging device, and attachment of fiducials or of bulky phantoms that are difficult to install and hinder surgery.

SUMMARY

It is an object of the technique presented herein to overcome at least some of the drawbacks of the prior art registration procedures. In particular, a registration technique for image data is needed which does not necessarily require the mounting of trackers on the imaging device nor the attachment of reference markings, such as fiducials and phantoms, to the object or the object tracker.

According to a first aspect, a method of registering image data of an object with at least one of a location and an orientation of the object is provided. The method comprises providing three-dimensional (3D) image data generated for the object, wherein the image data is representative of at least a portion of the object and of reference markings associated with the object, and wherein the reference markings have a known spatial relationship with a registration tracker adapted to be tracked by a navigation system. The method also comprises providing registration tracking data representative of at least one of a spatial location and a spatial orientation of the registration tracker, and further providing object tracking data representative of at least one of a spatial location and a spatial orientation of an object tracker adapted to be tracked by the navigation system, wherein the object tracker has a fixed spatial relationship with the object. From the registration tracking data and the object tracking data for a given point in time, the relative position between the registration tracker and the object tracker is calculated, and registered image data representative of at least one of the location and the orientation of the object is generated taking into account the spatial relationship between the reference markings and the registration tracker as well as the relative position between the registration tracker and the object tracker.

In one implementation, the step of generating the registered image data comprises determining at least one of the position and the orientation of the object tracker and of the registration tracker from the object tracking data and the registration tracking data, respectively, in relation to a first coordinate system associated with the navigation system, automatically determining the reference markings in the image data in relation to a second coordinate system associated with the image data, and performing a coordinate transfer of the coordinates of the object tracker from the first coordinate system into the second coordinate system via the registration tracker and the reference markings. For the coordinate transfer two dedicated transformations (also called mappings) may be performed. Alternatively, the two dedicated transformations may be combined into a single transformation, which transfers the coordinates directly into the second coordinate system.

The registration tracker and, optionally, the reference markings may have at least one of a loose (e.g., a non-invasive) and an arbitrary spatial relationship with the object during generation of the three-dimensional image data. For example, the registration tracker and, optionally, the reference markings may be located in a non-fixed manner (and, in a surgical scenario, in non-invasive manner) at or near the object. In other words, there is no need to attach the registration tracker and, optionally, the reference markings to the object, or to the imaging device. Moreover, the registration tracker may have an arbitrary spatial relationship with the object tracker. This means that the registration tracker can be placed independently from the object tracker, and in many instances the registration tracker will only temporarily be in use during an intra-navigation imaging procedure, while the object tracker will be in use during the entire navigation procedure.

An exemplary scenario involves the provision of multiple object trackers having fixed spatial relationships with multiple objects or multiple parts of the one and the same object. The multiple objects or multiple parts of one and the same object may be mutually displaceable. For each of the multiple object trackers dedicated object tracking data may be provided. It should be noted that various processes, operations and techniques described for a single object tracker herein may be applied to each individual object tracker (and object or object part) in case multiple object trackers are in use.

A registration device comprising the reference markings and the registration tracker and defining the known spatial relationship between the reference markings and the registration tracker may also be provided. The known spatial relationship may, for example, take the form of a known spatial relative position between the registration tracker and the reference markings of the registration device. At least one of the reference markings and the registration tracker may be detachable from the registration device.

In one imaging scenario, the registration device is at least one of loosely and arbitrarily co-located with the object. This co-location may involve that the reference markings are placed in an image volume of an imaging device upon generation of the three-dimensional image data by the imaging device. In this regard, the registration device may be located such that at least the reference markings are located in the image volume, while the registration tracker is visible to the navigation system (and optionally located outside the image volume).

The registration device may further comprise the object tracker, wherein the registration device defines the spatial relationship between the object tracker and the object.

According to a further variation, the registration device may comprise an adhesive layer to attach the registration device to the object, such that at least the reference markings are placed in an image volume of an imaging device upon generation of the image data by the imaging device.

The registration device may be positioned independently from the object tracker prior to generation of the image data. For example, the object tracker may be attached to the object already prior to the navigation procedure, and the registration device may be positioned at or near the object only temporarily in the context of an intra-navigation imaging step performed in the course of the navigation procedure. After the intra-navigation imaging procedure, the registration device may be removed, while the object tracker remains attached to the object. More generally, the provision of the registration tracking data may be stopped, and at least one of the registration tracker and the reference markings may be removed, after generation of the registered image data.

The provision of the object tracking data may be continued after generation of the registered image data (even though the provision of the registration tracking data may have stopped) to track any movements of the object. Based on the continued provision of the object tracking data, image data representative of at least one of the current location and the current orientation of the object may be updated and/or displayed taking into account the current object tracking data.

According to further variations, the given point in time at which the relative position between the registration tracker and the object tracker is calculated from the registration tracking data and the object tracking data may substantially coincide with or lay shortly before or after generation of the three-dimensional image data by the imaging device. During the generation of the three-dimensional image data, and optionally up to the given point in time for which the registration tracking data and the object tracking data are provided, the registration device and the object may remain stationary. The object can be any material object such as an industrial work piece, a body part, a surgical implant or a surgical instrument. Moreover, the image data may be generated using CT, a C-arm of an X-ray imaging system, MRI, ultrasonic imaging, or Position Emission Tomography (PET).

The technique presented herein may be realised in the form of software, in the form of hardware, or using a combined software/hardware approach. As regards a software aspect, a computer program product comprising program code portions for performing the steps presented herein when the computer program product is run on one or more computing devices is provided. The computer program product may be stored on a computer-readable recording medium such as a memory chip, a CD-ROM, a hard disk, and so on. Moreover, the computer program product may be provided for download onto such a recording medium.

According to a further aspect, a device kit for assisting the registration of image data of an object with at least one of a location and an orientation of the object is provided. The kit comprises a registration device comprising reference markings for an imaging device and a registration tracker adapted to be tracked by a navigation system, wherein the registration device defines a known spatial relationship between the reference markings and the registration tracker. The kit further comprises an object tracker adapted to be tracked by the navigation system, wherein the object tracker has an attachment mechanism (e.g., a clamping mechanism or a screwing mechanism) to be firmly attached to the object in a fixed spatial relationship with the object.

The registration device may have an essentially linear form and may be configured to receive the reference markings and the registration tracker at opposite ends thereof in a fixed or detachable manner. In one implementation, the registration device is configured to be loosely associated with the object. For example, the registration device may lack any attachment mechanism and may simply be configured to be put at or near the object. Further, the registration device may have three or more fingers or tabs extending in different directions. Each finger or tab may constitute or carry one or more of the reference markings.

In one implementation, the registration device may be configured to be mounted on the object. For example, the registration device may comprise a flexible substrate and an adhesive layer to attach the substrate to the object.

Further, the registration device may include emitters which are attached to the flexible substrate at connection points. For example, the emitters can be Light Emitting Diodes (LEDs) or passive reflectors which are bonded to or soldered on the flexible substrate. Further, the connection points may be soldering points for electrically connecting the emitters to a power source. In one implementation, the emitters or the connection points may function as the reference markings for the imaging device. Further, small ball-like reference markings may be attached to the substrate in a predetermined spatial relationship to the emitters.

According to a further aspect, the registration device may comprise at least three emitters (or groups of at least three emitters) at predetermined locations. In this regard, each emitter may be in a fixed relation to its neighbouring emitter. Further, the emitters can be adapted to be tracked by the navigation system. In a further implementation, the emitters may be connected to a power source by flexible conductive circuits. The power source can be a battery, an accumulator, or any other external power source. Alternatively, the power source may be an internal power source which is mounted on or within the registration device.

Still further, a navigation system for registering image data of an object with at least one of a location and an orientation of the object is provided. The system comprises an interface adapted to receive three-dimensional image data generated for the object, wherein the image data are representative of at least a portion of the object and of reference markings associated with the object, and wherein the reference markings have a known spatial relationship with a registration tracker adapted to be tracked by the navigation system. The navigation system further comprises a processor adapted to provide registration tracking data representative of at least one of a spatial location and a spatial orientation of the registration tracker and object tracking data representative of at least one of a spatial location and a spatial orientation of an object tracker adapted to be tracked by the navigation system, wherein the object tracker has a fixed spatial relationship with the object. The processor is further adapted to calculate from the registration tracking data and the object tracking data for a given point in time the relative position between the registration tracker and the object tracker, and to generate registered image data representative of at least one of the location and the orientation of the object taking into account the spatial relationship between the reference markings and the registration tracker and the relative position between the registration tracker and the object tracker.

The system may further comprise an imaging device for generating the image data, such as a CT imaging device, a C-arm of an X-ray imaging system, an MRI device or an ultrasonic imaging device. Still further, the system may comprise the device kit as discussed herein.

In one implementation, the system further comprises a registration device including the reference markings for an imaging device and the registration tracker, wherein the registration device defines a known spatial relationship between the reference markings and the registration tracker, and wherein the registration device includes the object tracker. In this regard, the registration device may be configured as discussed herein.

Still further, a registration device for assisting the registration of image data of an object with at least one of a location and an orientation of the object is provided. The registration device comprises reference markings for an imaging device and a registration tracker adapted to be tracked by a navigation system, wherein the registration device defines a known spatial relationship between the reference markings and the registration tracker. The registration device further includes an object tracker adapted to be tracked by the navigation system, and a flexible substrate adapted to be attached to the object, wherein the registration tracker and the object tracker comprise at least three emitters attached to the substrate at predetermined locations.

In one implementation, the registration tracker may be operative during registration and the object tracker may be operative after registration, wherein the emitters of the registration tracker and of the object tracker may be configured to be illuminated independently.

Still further, the registration device can also be configured as discussed herein.

BRIEF DESCRIPTION OF THE DRAWINGS

Further aspects and advantages of the technique presented herein will become apparent from the following description of preferred embodiments and the drawings, wherein.

DETAILED DESCRIPTION

In the following description of preferred embodiments, for purposes of explanation and not limitation, specific details are set forth (such as particular components of a navigation system and particular sequences of steps) in order to provide a thorough understanding of the registration technique presented herein. It will be apparent to one skilled in the art that this technique may be practiced in other embodiments that depart from these specific details. For example, while the following embodiments will primarily be described in context with surgical navigation, the present registration technique can also be used in other fields of image-assisted navigation. Moreover, while some of the embodiments will deal with intra-navigation (e.g., intra-operative) imaging procedures, the registration technique presented herein may also be used in certain pre- or post-navigation imaging scenarios.

Moreover, those skilled in the art will appreciate that the services, functions and steps explained herein below may be implemented using software functioning in conjunction with a programmed microprocessor, an Application Specific Integrated Circuit (ASIC), a Digital Signal Processor (DSP) or a general purpose computer. It will also be appreciated that while the following embodiments will primarily be described in context with methods and devices, the invention may also be embodied in a computer program product as well as in a system comprising a computer processor and a memory (or any other computer-readable medium) coupled to the processor, wherein the memory is encoded with one or more programs that may perform the services, functions and steps disclosed herein.

Figure 1:
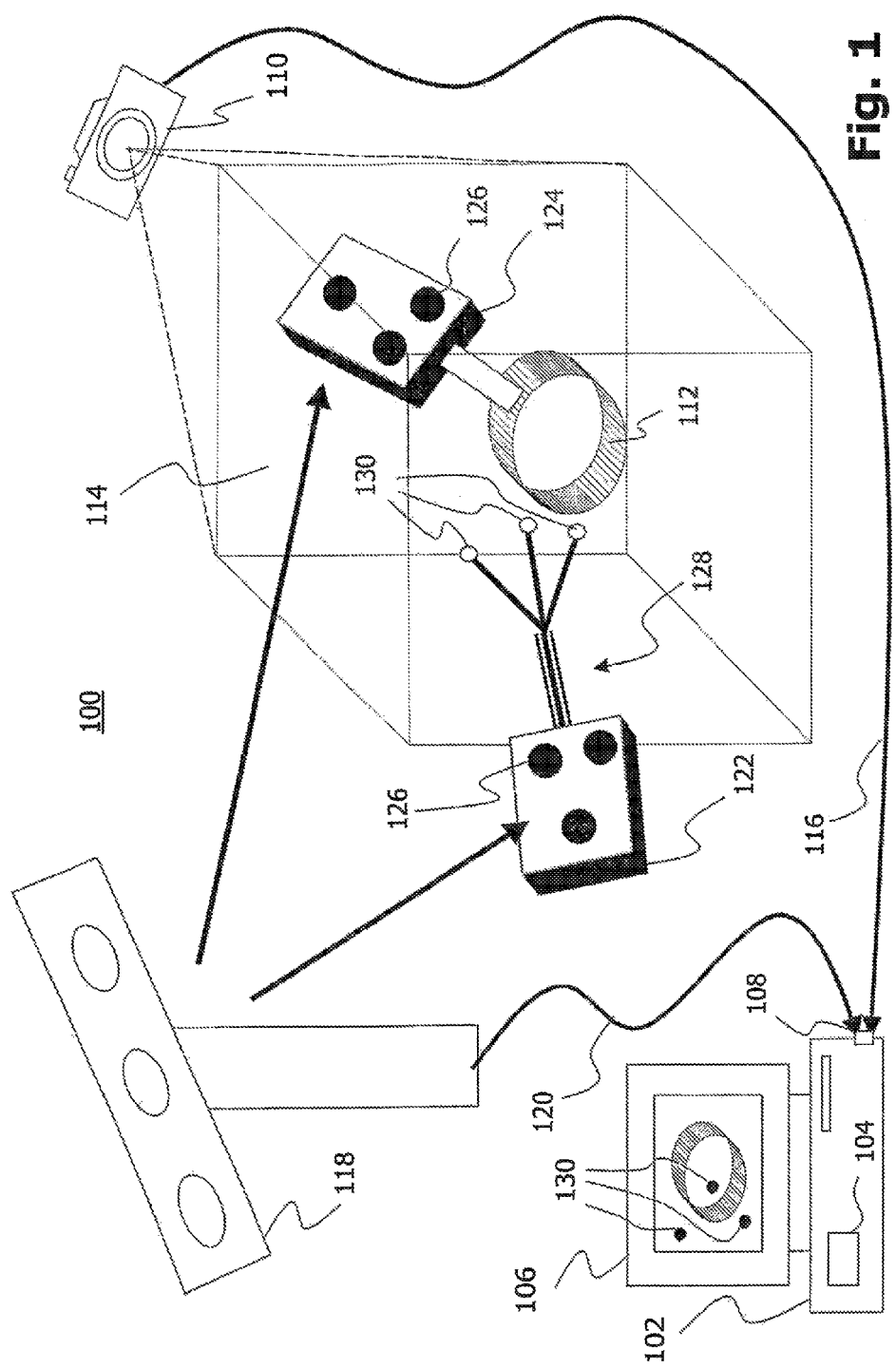
FIG. 1 schematically illustrates embodiments of a navigation system and of a particular navigation scenario.

FIG. 1 schematically illustrates embodiments of a navigation system 100 and of a particular navigation scenario. As shown in FIG. 1, the navigation system 100 comprises as a central component a navigation computer 102. The navigation computer 102 includes a navigation processor 104 adapted to process, inter alia, navigation-related data, a display device 106 adapted to visualize the results of the navigation-related data processing operations of the processor 104, and an interface 108 adapted to receive at least some of the navigation-related data processed by the processor 104.

An imaging device 110 is configured to generate three-dimensional image data, such as CT or MRI data, of an object 112 located in an image volume 114 of the imaging device 110. The imaging device 110 is coupled via a wired or wireless connection 116 to the interface 108 of the navigation computer 102 to transmit the image data to the processor 104.

The navigation system 100 also comprises a sensor unit 118 coupled via a wired or wireless connection 120 to the interface 108 of the navigation computer 102. Via the connection 120, the processor 104 receives sensor data that are processed by the processor 104 to generate tracking data as will be described in more detail below.

The sensor unit 118 may be configured as is generally known in the art. For example, the sensor unit 118 may comprise a source of infrared radiation configured to illuminate a navigation volume in which the object 112 is located. The navigation volume may generally differ from the image volume 114. The sensor unit 118 additionally comprises two or more infrared sensors (e.g., infrared cameras) configured to detect any infrared radiation reflected from within the navigation volume, and to transmit the corresponding sensor data via the connection 106 to the navigation computer 102. In a different implementation, the source of infrared radiation may be omitted from the sensor unit 118 and active infrared transmitters may be located in the navigation volume.

Instead of in the infrared spectrum, the navigation system 100 may operate in any other portion of the electromagnetic spectrum, or the navigation system 100 may be based on ultrasonic technologies. Alternatively, or in addition, the operation of the navigation system 100 may be based on video cameras tracking a specific patterns or three-dimensional bodies.

Active or passive (reflective) radiation emitters of the navigation system 100 are mounted on two trackers 122, 124 that are both located within the navigation volume. In the exemplary scenario illustrated in FIG. 1, each tracker 122, 124 comprises at least three such emitters 126. Instead of, or in addition to, radiation emitters 126, the trackers 122, 124 may also comprise one or more patterns or three-dimensional bodies for being tracked by video cameras.

The first tracker (or registration tracker) 122 belongs to a registration device 128 which further comprises (at least) three reference markings 130 capable of being detected by the imaging device 110 when located in the image volume 114. The reference markings 130 may be realized in various forms as will be described in more detail below. For example, the reference markings 130 may be configured as an array of fiducial points (e.g., metal balls) as illustrated in FIG. 1, as fiducial rods or as any other fiducial structure of known geometry. The reference markings 130 may also take the form of phantoms. The reference markings 130 have a known spatial relationship with the registration tracker 122. This spatial relationship is defined by a rigid and preferably elongated (e.g., linear) portion of the registration device 128 connecting the reference markings 130 and the registration tracker 122.

The second tracker (or object tracker) 124 is fixedly attached to the object 112. In other words, the object tracker 124 has a fixed spatial relationship with the object 112. This fixed spatial relationship may be maintained by screwing, clamping or otherwise attaching the object tracker to the object 112. The relationship should be such that the object tracker 124 moves together with the object 112 when the object 112 is subjected to a rotational, translational or any other movement.

Figure 2:
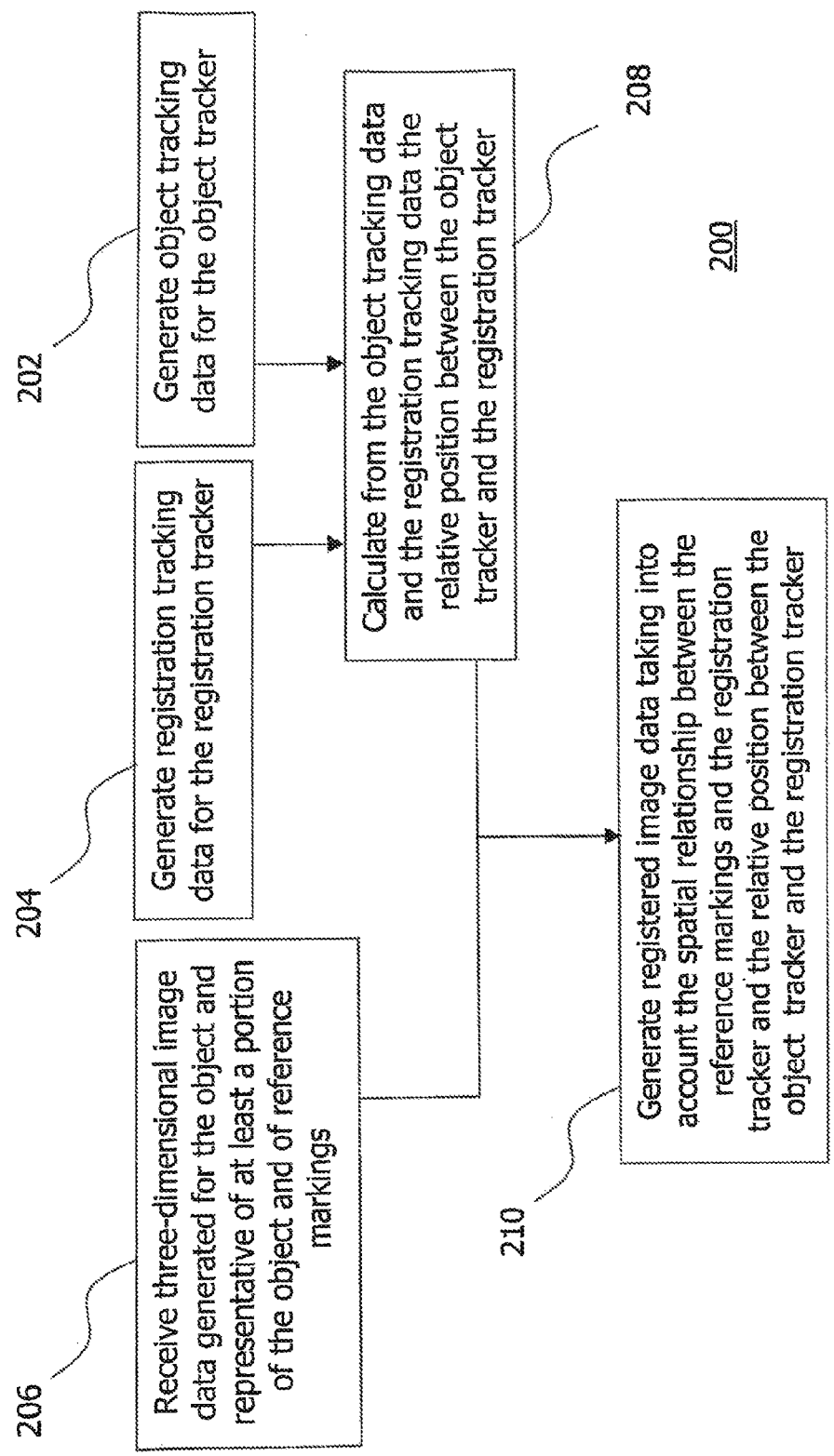
FIG. 2 shows a flow diagram according to a method embodiment.

In the following, the operation of the navigation system 100 illustrated in FIG. 1 will be described with reference to the schematic flow diagram 200 of FIG. 2. The flow diagram 200 illustrates a method embodiment of a technique for registering image data of the object 112 with the current location and orientation of the object 112 in the navigation volume.

As a first preparatory measure, the object 112 is placed within the navigation volume and the object tracker 124 is attached to the object 112 such that the object tracker 124 (i.e., the emitters 126 of the object tracker 124) remain visible to the sensor unit 118 in the navigation volume. As a second preparatory measure, the registration device 128 is placed at or in the vicinity of the object 112. In this regard care is taken that the reference markings 130 of the registration device 128 will be located within the image volume 114 and the registration tracker 122 with its emitters 126 remains visible to the sensor unit 118. This means that similar to the object tracker 124, the registration tracker 122 is also placed in the navigation volume.

In one scenario, the first preparatory measure precedes the second preparatory measure such that during an ongoing navigation procedure based on a tracking of the object tracker 124 the second preparatory step is performed at least once for an intra-navigation imaging procedure. The registration device 128 may then be removed after the intra-navigation imaging procedure and successful registration of the image data thus obtained, while the navigation procedure based on a tracking of the object tracker 124 may continue without interruption.

In an exemplary surgical scenario, the registration device 128 may thus be in use only temporarily during intra-operative imaging procedures while the object tracker 124 is continuously tracked during the entire surgical operation. It will, of course, be appreciated that the registration technique presented herein can also be used in other navigation scenarios.

In the intra-navigation imaging procedure discussed above, the sensor unit 118 will, in addition to the pre-attached object tracker 124, thus also detect the registration tracker 122 as soon as the registration tracker 122 has been associated with the object 112 in the navigation volume and the registration tracker 122 has been activated. This means that the sensor unit 118 will then transmit sensor data indicative of the positions of the patient tracker 124 and the registration tracker 122 via the connection 120 and the interface 108 to the processor 104. Based on the sensor data received from the sensor unit 118, the processor 104 generates object tracking data for the object tracker 124 as well as registration tracking data for the registration tracker 122 in steps 202 and 204 of FIG. 2. These tracking data are indicative of the positions of the object tracker 124 and the registration tracker 122 within a coordinate system associated with the navigation volume (and thus also associated with the object tracker 124 continuously tracked in the navigation volume).

Once both the object tracker 124 and the registration tracker 122 can be tracked by the navigation system 100, an intra-operative scan (e.g., a CT scan) is performed by the imaging device 110 to image the object 112 as well as the reference markings 130 located in the image volume 114. Then, in step 206, the three-dimensional image data generated by the imaging device 110 are received via the connection 116 and the interface 108 by the processor 104. The image data are representative (i.e., contain) of the object 112 and the reference markings 130. As a further measure, the processor 104 assigns a three-dimensional coordinate system to the image data and detects the position and orientation of the reference markings 130 within this coordinate system. Simultaneously, the position and orientation of the registration tracker 122 and of the object tracker 124 in the coordinate system of the navigation volume are detected by the processor 104 for a given point in time close to the imaging procedure, and the processor 104 calculates in step 208 from the associated object and registration tracking data the relative position between the object tracker and the registration tracker 122 in the coordinate system of the navigation volume.

In a next step 210, registered image data are generated by the processor 104. The registered image data are generated taking into account the spatial relationship between the reference markings 130 and the registration tracker 122 (as a priori known to the navigation system 100) as well as the relative position between the object tracker 124 and the registration tracker 122. Once the registered image data have been generated in step 210, the registration device 128 can be removed and the provisioning of the registration tracking data can be stopped. The further navigation procedure may continue based on the registered image data and the object tracking data continuously provided by the object tracker 124 until the end of the navigation procedure. As illustrated in FIG. 1, the current location and the current orientation of the object 112 may be visualized on the display device 106 for navigation purposes.

Generation of the registered imaged data in step 210 may be performed in various ways. For example, in a first step the position and orientation of the registration tracker 122 and of the object tracker 124 are detected by the navigation system with respect to the coordinate system of the navigation volume just prior to the image acquisition step, during the image acquisition step or just after the image acquisition step. In a next step the position and orientation of the reference markings 130 are automatically determined in the image data with respect to the coordinate system of the image volume. Since the geometry of the reference markings 130 with respect to the registration tracker 122 is known to the navigation system, the position and orientation of the image data are known with respect to the registration tracker 122. Further, since the relative position and orientation of the object tracker 124 with respect to the registration tracker 122 have been recorded by the navigation system, the position and orientation of the image data are known with respect to the object tracker 124. Due to this information the coordinates of the object tracker 124 representing the position and orientation of the object in the navigation volume are transferred into the coordinate system of the image volume and correlated with the image data via the registration device 128. As a result of this transformation, the image data have been registered with the object tracker 124, and the further visualization of the image data can be dynamically adapted to the current location and the current orientation of the object 112 in the navigation volume as determined via the object tracker 124.

As has become apparent from the above description of an exemplary navigation scenario, the registration technique presented herein is completely independent from the kind of imaging device 110 and even works if the imaging device 110 is replaced by another imaging device for a further imaging procedure during an ongoing navigation procedure. This independence is a result of the fact that no defined spatial relationship between the three-dimensional image data and the imaging device 110 is necessary. In other words, the location and orientation of the imaging device 110 do not have to be tracked for image registration purposes, as the registration technique presented herein is capable of directly correlating the image data with the object tracker 124. Further, no prior adaptation or calibration of the imaging device 110 is required for the registration technique presented herein.

Additionally, a fixed spatial relationship between the object tracker 124 and/or the object 112 on the one hand and any reference markings (such as imaging phantoms or fiducials) on the other hand is no longer necessary with the result that a time consuming attaching and detaching of reference markings to the object tracker 124 and/or the object 112 itself can be omitted. Consequently, the object tracker 124 can be re-positioned during the ongoing navigation procedure and the registration can be performed easily after the re-positioning.

As a further advantage, the registration device 128 itself can be realized as a freely movable device that is not subject of any (invasive) attachment requirements. The registration device 128 can thus easily temporarily be positioned in the vicinity of the object 112 during the imaging and registration procedures. After registration, the registration device 128 can easily be removed without having to be detached, and will not hinder the further navigation or any other procedure. In one scenario, the registration device 128 may be non-invasively attached at or near the object 112, but not as firm as the object tracker 124 (which typically is attached to the object 112 in an invasive manner).

Figure 3:
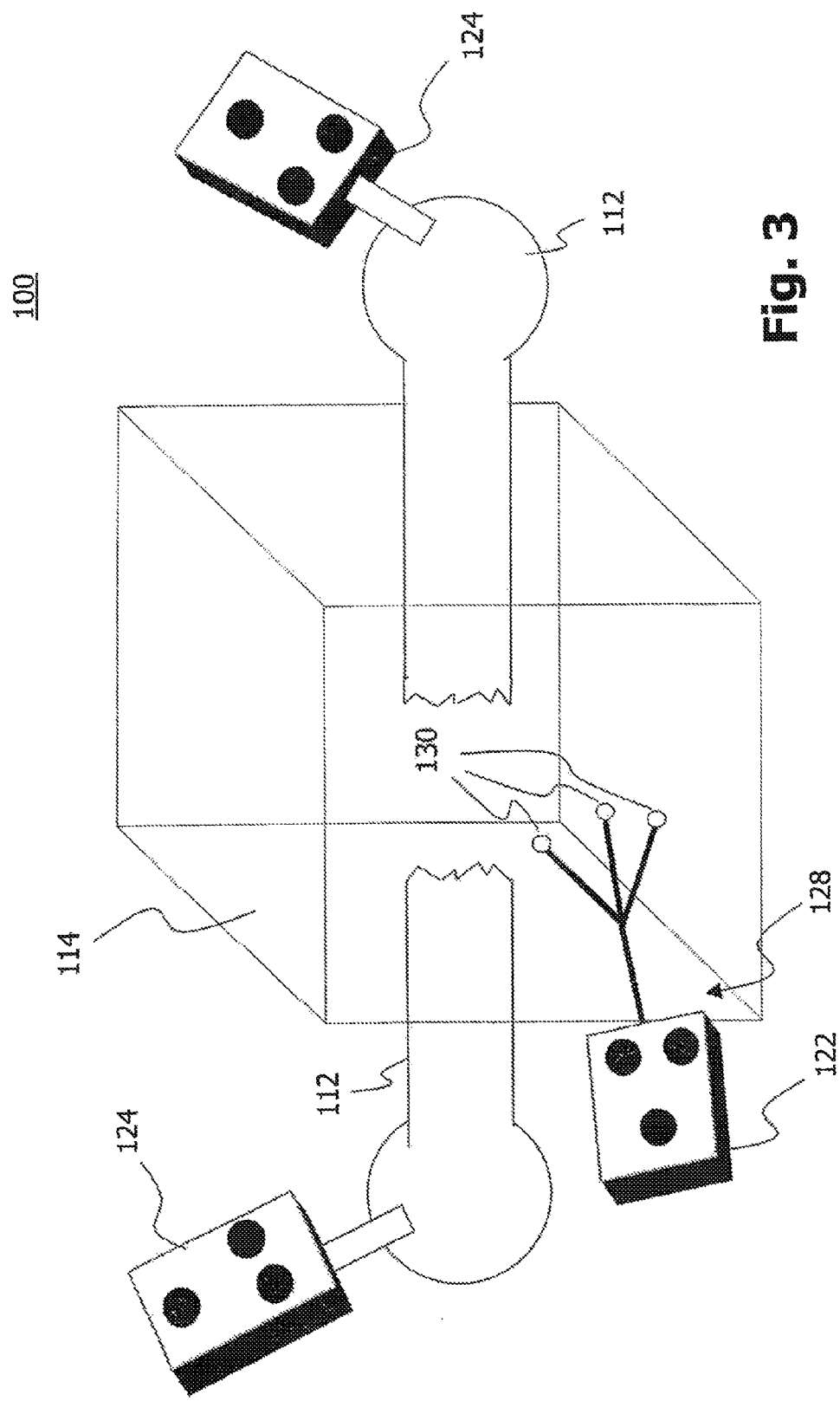
FIG. 3 schematically illustrates an embodiment of a further navigation scenario, FIGS. 4 to 7 schematically show four embodiments of a registration device.

Reference is now made to FIG. 3 which shows a further navigation scenario in which two object trackers 124 are utilized in combination with the registration device 128. The navigation scenario of FIG. 3 pertains to a surgical operation in which two parts of a broken femur 112 have to be re-positioned, and in which the re-positioning is to be monitored by intra-operative imaging procedures. In FIG. 3, some of the components of the navigation system 100 have been omitted for clarity purposes, and the same reference numerals designate the same elements as in FIG. 1.

As shown in FIG. 3, to each part of the broken femur 112 a dedicated object tracker 124 is attached. The first object tracker 124 is positioned close to the femur neck, and the second object tracker 124 is positioned at the opposite, distal part of the femur 112. Obviously, the registration procedure could also be performed in navigation scenarios with three or more object trackers 124.

In the navigation scenario of FIG. 3, both parts of the femur 112 are registered independently from each other with the corresponding image data and are also tracked independently from each other during the surgical operation. Prior to each imaging procedure, the registration device 128 is temporarily put close to the surgical site such that the reference markings 130 are located within the image volume 114 and the registration tracker 122 is located together with both object trackers 124 within the navigation volume as discussed above with reference to FIGS. 1 and 2. The actual registration procedure will be performed individually for the registration device 128 and each single object tracker 124 in the same manner as described above in relation to the flow diagram 200 of FIG. 2.

It will be appreciated that the registration technique presented herein can also be utilized in surgical navigation scenarios different from trauma where multiple anatomical body parts need to be registered and tracked independently. As one example, the surgical field of CMF can be mentioned, in which two object trackers will be attached to an upper jaw and a lower jaw, respectively, of a patient. Instead of or in addition to tracking anatomical body parts, medical instruments and medical implants can be tracked also provided that object trackers 124 are attached to them. The corresponding tracking data thus obtained may then be used as a basis for the registration technique presented herein as generally discussed above.

In the following, several embodiments of the registration device 128 illustrated in FIGS. 1 and 3 will be described in more detail. It will be appreciated that the registration device 128 can be used either separately or as part of a device kit additionally comprising one or more object trackers (i.e., one or more trackers configured to be attached to an object of interest). A common aspect of the various embodiments described hereinafter is the fact that the registration device 128 is configured to assume a stable position when associated with the object 112 without the need for a specific attachment mechanism. Therefore, in the following embodiments, the registration device 128 always has one or more predefined sides that allow the registration device 128 to be placed in a stable, predefined manner on a given plane (e.g., on an operating table next to the patient) or on a specific object such as an anatomical body part (e.g., a spinal column of a patient). It should be noted that in other embodiments not illustrated in the drawings, the registration device 128 may comprise a mechanism for loosely (e.g., non-invasively) attaching the registration device to the patient or in the vicinity of the patient. In a further embodiment, the registration device may be a (e.g., flexible) mask or sheet which can be adhered to the skin of the patient.

Figure 4:
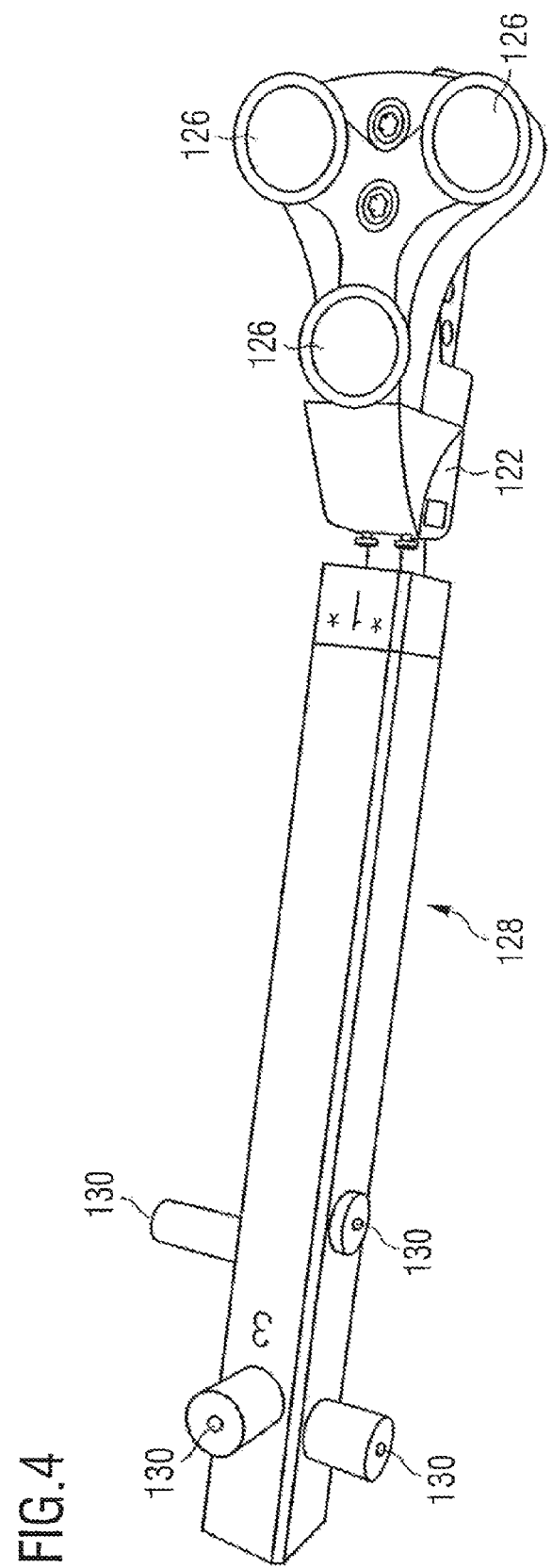

FIG. 4 illustrates a first embodiment of the registration device 128. The registration device shown in FIG. 4 comprises an elongated rod-like member made of radiolucent material and having a first end for detachably receiving the registration tracker 122 with its infrared emitters 126 as well as an opposite, second end with a plurality of fingers or projections. The projections generally extend radially from the rod-like member and comprise metal balls on their distal ends. The metal balls (or any other opaque structures) are made from tungsten and constitute the reference markings 130 (i.e., the fiducials) for the imaging procedure.

As becomes apparent from FIG. 4, the protrusions extend from only three of the four sides of the rod-like member. In other words, there is no projection on the "back" side of the registration device 128 so that the registration device 128 can be placed with its back side in a stable manner on a flat surface. Moreover, it also becomes apparent from FIG. 4 that the registration device 128 does not comprise any specific attachment mechanism, as the registration device 128 is not designed to be attached to any specific component (such as the object 112 or the imaging device 110 in FIG. 1).

Figure 5:
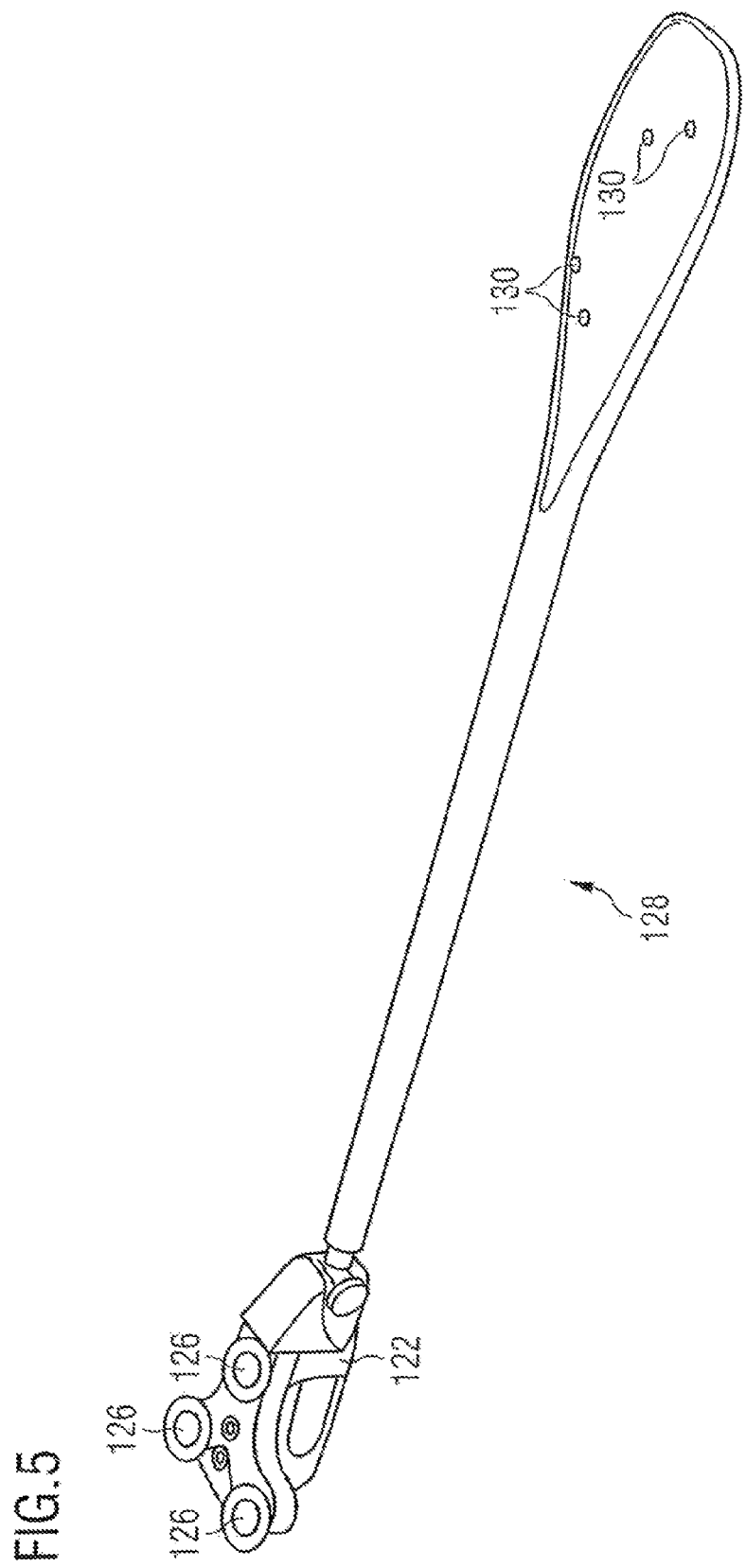

FIG. 5 illustrates a second embodiment of the registration device 128. The registration device 128 has an elongated form with the registration tracker 122 and its emitters 126 being located at a first end thereof. Spoon-like support for a three-dimensional arrangement of ball-like reference markings 130 (similar to the first embodiment) is located at the opposite, second end of the registration device 128.

The ball-like reference markings 130 illustrated in FIGS. 4 and 5 have a comparatively small size. For this reason, their impact as artefacts in the image data is comparatively low, and they can be easily located in the image data using automatic procedures.

Figure 6:
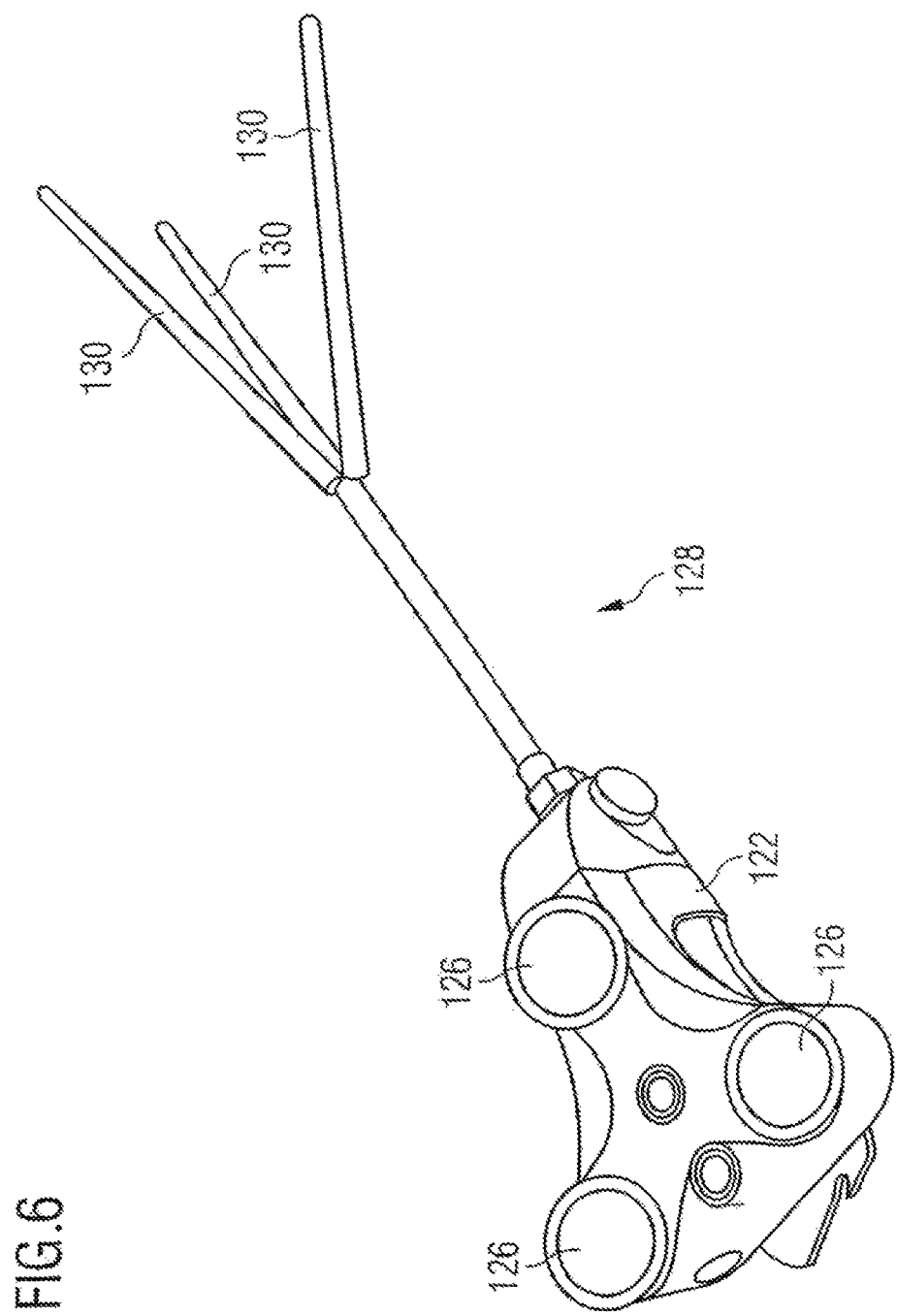

FIG. 6 shows a third embodiment of the registration device 128. Similar to the first and second embodiments shown in FIGS. 4 and 5, respectively, the registration device 128 is of an elongated form and comprises the registration tracker 122 with its emitters 126 at one end thereof. The other end of the registration device 128 has a fork-like shape with three rods or fingers diverting from each other in a direction away from the registration tracker 122. These rods are made from a material such as tungsten which shows up in the image data generated by the imaging device 110. In other words, in the embodiment of FIG. 6 the rods constitute the reference markings.

Figure 7:
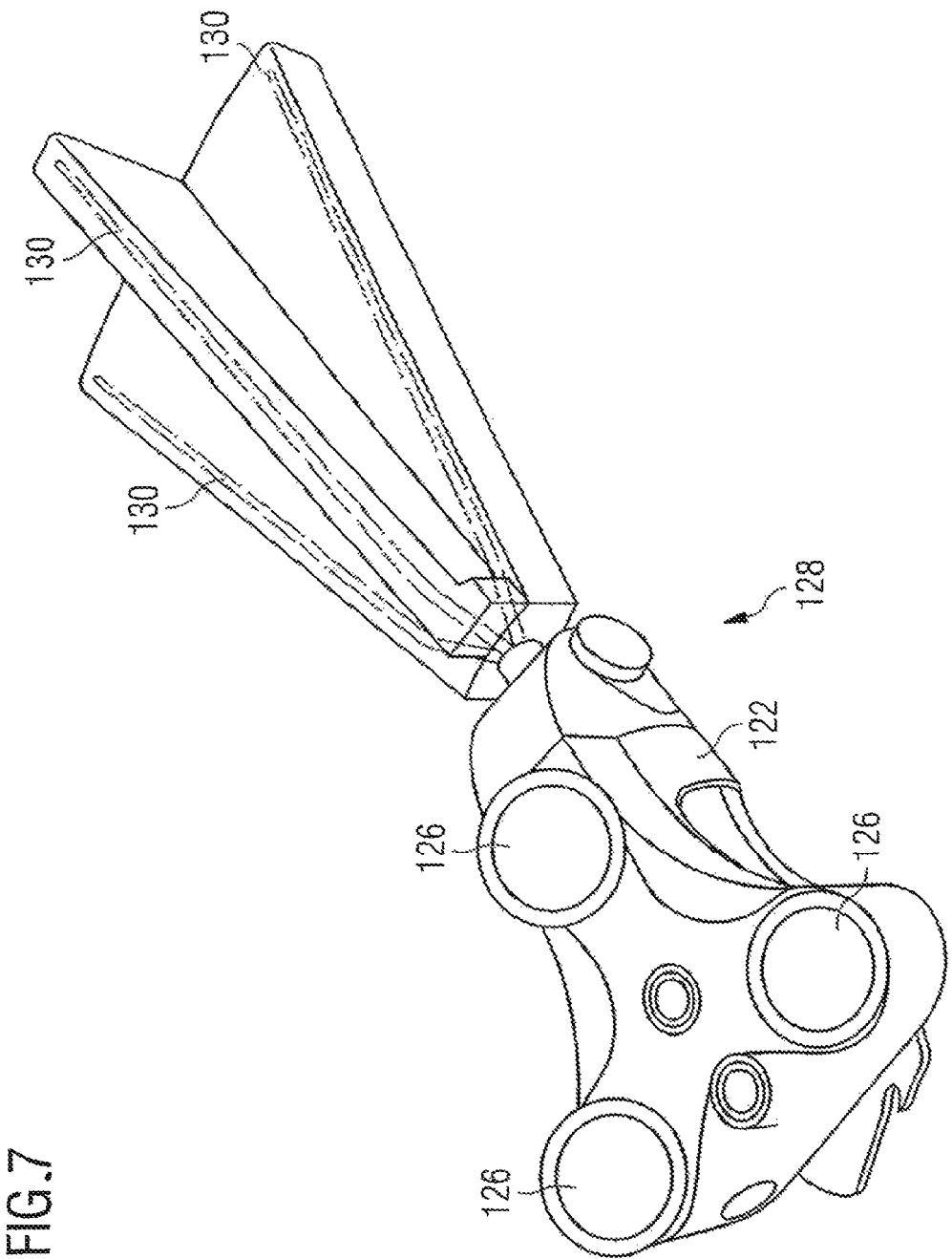

FIG. 7 shows a fourth embodiment of the registration device 128 similar to the registration device of the third embodiment illustrated in FIG. 6. The registration device 128 shown in FIG. 7 also comprises three fingers made of (thinner) wire pieces and embedded in dedicated tabs of a radiolucent material such as plexiglas.

Similar to the registration device 128 of FIG. 4, the two registration devices 128 of FIGS. 6 and 7 likewise have at least one predefined side for being placed in a stable manner on a planar surface.

The technical advantage of the two embodiments illustrated in FIGS. 6 and 7 is the fact that the respective registration device 128 can also be used in combination with an imaging device 110 which scans slices or layers like a CT imaging device or an imaging device which scans the two-dimensional projection images like a C-arm of a three-dimensional X-ray imaging device. Using reference markings 130 having an extended (e.g. fork-like geometry) as the ones illustrated in FIGS. 6 and 7 ensures that in many image layers at least parts (points) of the individual fingers will be sufficiently recognizable for determining the orientation of reference markings in the coordinate system of the three-dimensional image data.

A further advantage of the extended geometries of the reference markings 130 is the fact that they can easily be placed within the image volume as the registration can also probably be carried out in cases in which only portions of the extended reference markings 130 are imaged. As a result, the imaging volume (e.g., the scanning volume) can be comparatively small (in the case ball-like reference markings are used, at least three balls have to be completely imaged). Moreover, using extended reference markings 130, non-visible portions of the reference markings 130 can be re-constructed based on a priori knowledge of their geometry. This means that the registration technique can also successfully be performed in the case of a lower image quality. Moreover, any (undesired) movement of the registration device 128 during imaging can easily be detected as the extended reference markings 130 will the appear in the image data in a distorted manner. Using ball-like reference markings, dedicated algorithm might be required to detect that the mutual positions of the ball-like reference markings are not consistent.

Figure 8:
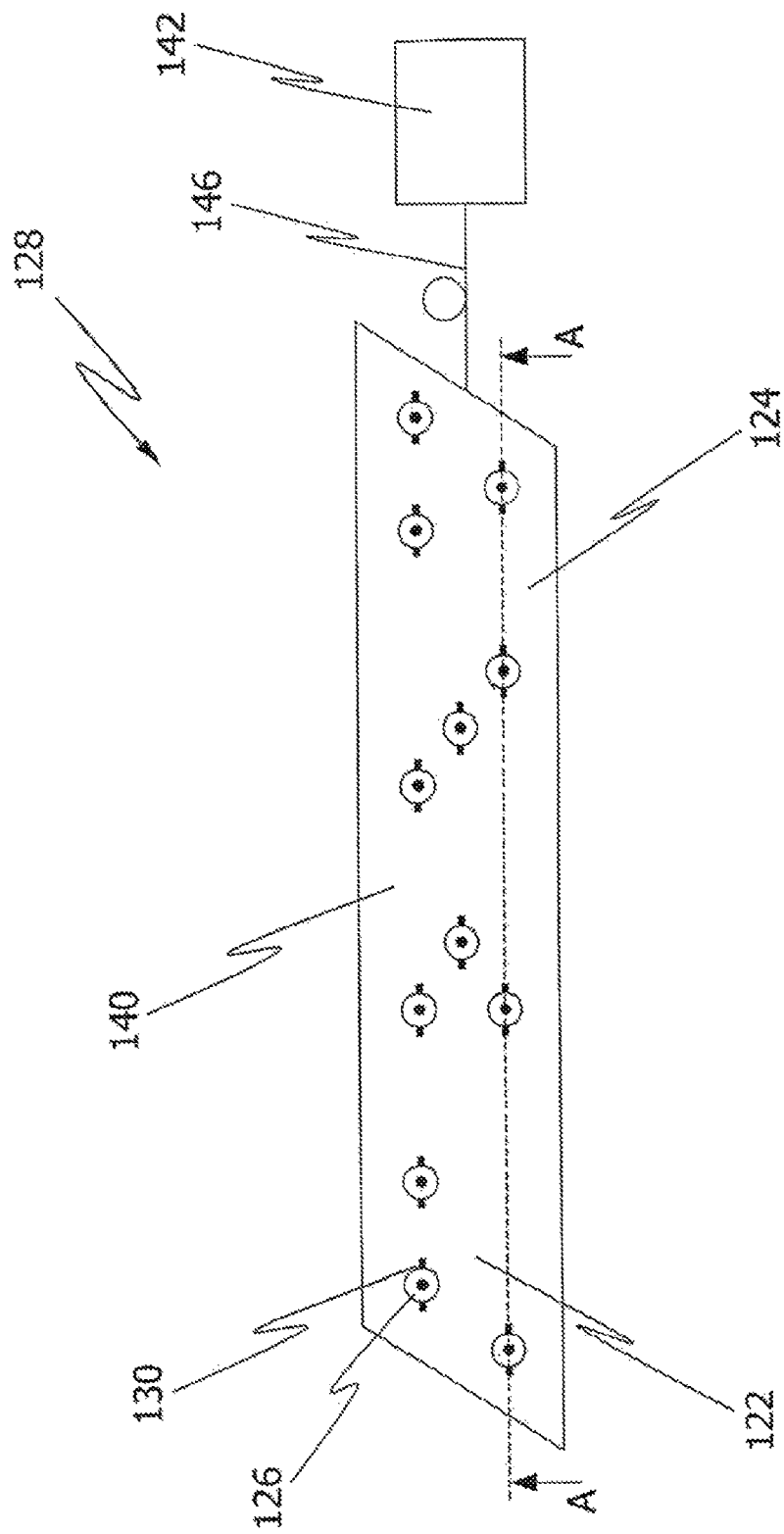
FIG. 8 schematically illustrates a fifth embodiment of a registration device.
Figure 9:
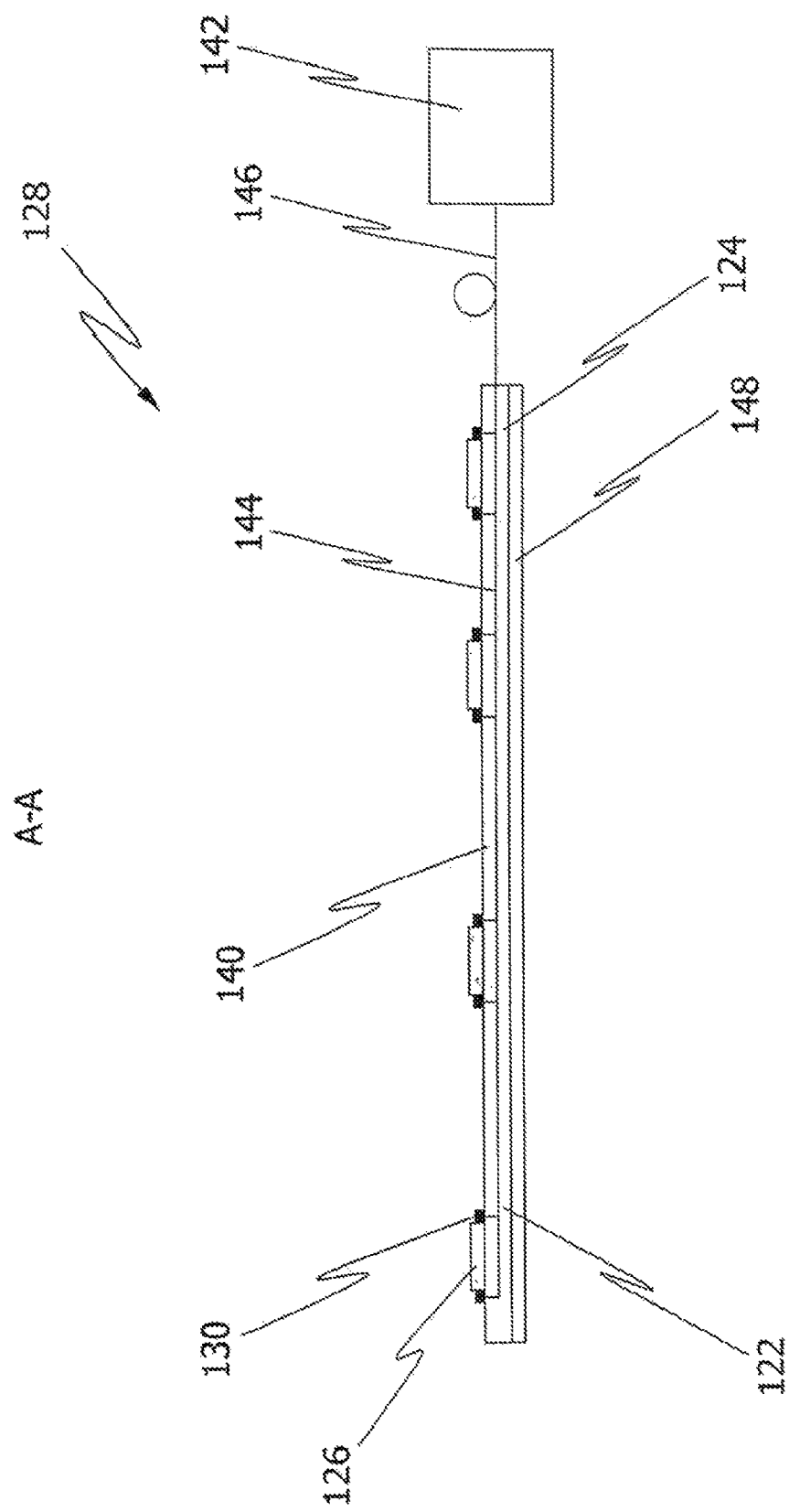
FIG. 9 schematically shows a cross sectional view of the registration device illustrated in FIG. 8.

FIGS. 8 and 9 show a fifth embodiment of the registration device 128. In contrast to the registration devices of the first to fourth embodiments illustrated in FIGS. 4 to 7, the registration device 128 shown in FIG. 8 includes the registration tracker 122 and the object tracker 124. The registration device 128 is in the form of an elongated flexible mask or sheet. Even if FIG. 8 shows an elongated sheet 128, the sheet can have any suitable shape, such as a curved, an angular, a zick-zack or any other arbitrary shape. The sheet 128 includes a flexible sheet or substrate 140 which defines the registration tracker 122 and the object tracker 124. Thus, both the registration tracker 122 as well as the object tracker 124 have a sheet or substrate 140 to be attached to the object 112. The flexible sheet 128 can be formed from any suitable surgically acceptable sheet material such as industry standard flexible FR4 sheet materials or any other polymeric materials such as polyimide, polyester, and the like.

Further, emitters such as infrared emitters 126 are attached to the flexible substrate on one surface thereof by connection points 130. The connection points 130 are soldering points to electrically connect the emitters 126 to a power source 142 by flexible conductive circuits 144. The emitters 126 are all powered by the power source 142 such as a battery pack 142 which is attached to the flexible sheet 128 by a cable 146. Either the emitters 126 or the connection points 130 function as the reference markings 130 for the imaging device 110. Since the registration tracker 122 is a part of the sheet 128 and the emitters 126 are fixed to the surface of the sheet 128 by the connection points 130, the registration device 128 defines the known spatial relationship between the reference markings 130 and the registration tracker 122. Alternatively, small ball-like reference markings (not shown) may be attached to the flexible sheet 128 in a predetermined spatial relationship to the emitters. Hence, each of the registration tracker 122 and the object tracker 124 includes emitters 126 attached to the substrate 140 at predetermined locations.

FIG. 9 illustrates a cross sectional view of the registration device 128 shown in FIG. 8 along the line A-A. As shown in FIG. 9, the registration device 128 comprises an adhesive layer 148 to attach the flexible substrate 140 to the object 112. The layer 148 of light adhesive on the underside of the flexible substrate 140 is used to stick the registration device 128 onto the skin of a patient 112. For this reason, the object tracker 124 has a fixed spatial relationship with the object 112. The adhesive may be any adhesive suitable for human contact. For example, a contact adhesive which can be removed without damage to the patient's skin, such as surgical adhesives, patch adhesives or any other similar adhesives which are suitable for use in contact with a human skin.

For simplicity, the wiring from the battery pack 142 to each of the emitters 126 is not shown in detail in FIGS. 8 and 9. However, each emitter 126 is connected to the battery pack 142 by a positive flexible conductive circuit and a negative conductive circuit (not shown). The conductive circuits 144 are formed within the substrate 140 and are formed from any suitable conductive material, such as copper, aluminium, silver, and the like. Alternatively, the conductive circuits 144 may be formed directly on the surface of the substrate 140. For example, conductive inks can be used to print the conductive circuits 144 onto the substrate 140.

Each emitter 126 is capable of being independently illuminated such that the navigation system 100 can determine the position of each individual emitter 126 on the registration device 128. Further, each emitter 126 is in a known relationship to its neighbouring emitter 126 and the emitters 126 can form groups of at least three emitters 126 at predetermined locations on the substrate 140 of the registration device 128. These groups of emitters 126 may form different formations regarding the position of each emitter 126 within one group. Thus, the emitters 126 of each group can form a defined array, as shown in FIG. 8. For example, these arrays of emitters 126 can have a L-shape, an I-shape, a triangle shape or a rectangle shape. The emitters 126 are visible to the sensor unit 118 of the navigation system 100 for tracking and therefore for registration as described at the above embodiments of the registration and tracking technique.

Before the registration process, all emitters 126 are illuminated in an initial identification process. The illuminated emitters 126 are then detected by the sensor unit 118 for determining the position of the emitters 126 and, consequently, the corresponding position of the reference markings 130. Once the registration device 128 which is attached to the object 112 is scanned along with the object 112, the reference markings 130 in form of the emitters 126 or the connection points 130 are detected within the image data of the imaging device 110.

When the registration process is completed, the registration device 128 shown in FIGS. 8 and 9 can be used as object tracker. Hence, the registration tracker 122 of the registration device 128 is operative during registration and the object tracker 124 of the registration device 128 is operative after registration. Thereby, the emitters 126 of the registration tracker 122 and of the object tracker 124 may be configured to be illuminated independently. In this case, any arbitrary group of emitters 126 detected by the sensor unit 118 allows the tracking of the object 112, even if this group of emitters 126 is not detected within the image volume 114 of the imaging device 110. Thus, it is not required to detect all markers of the entire registration device 128 by the sensor unit 118 during object tracking. Alternatively, the registration device 128 can be removed, such that another object tracker 124 as shown, e.g., in FIG. 1 can be used for tracking.

Figure 10:
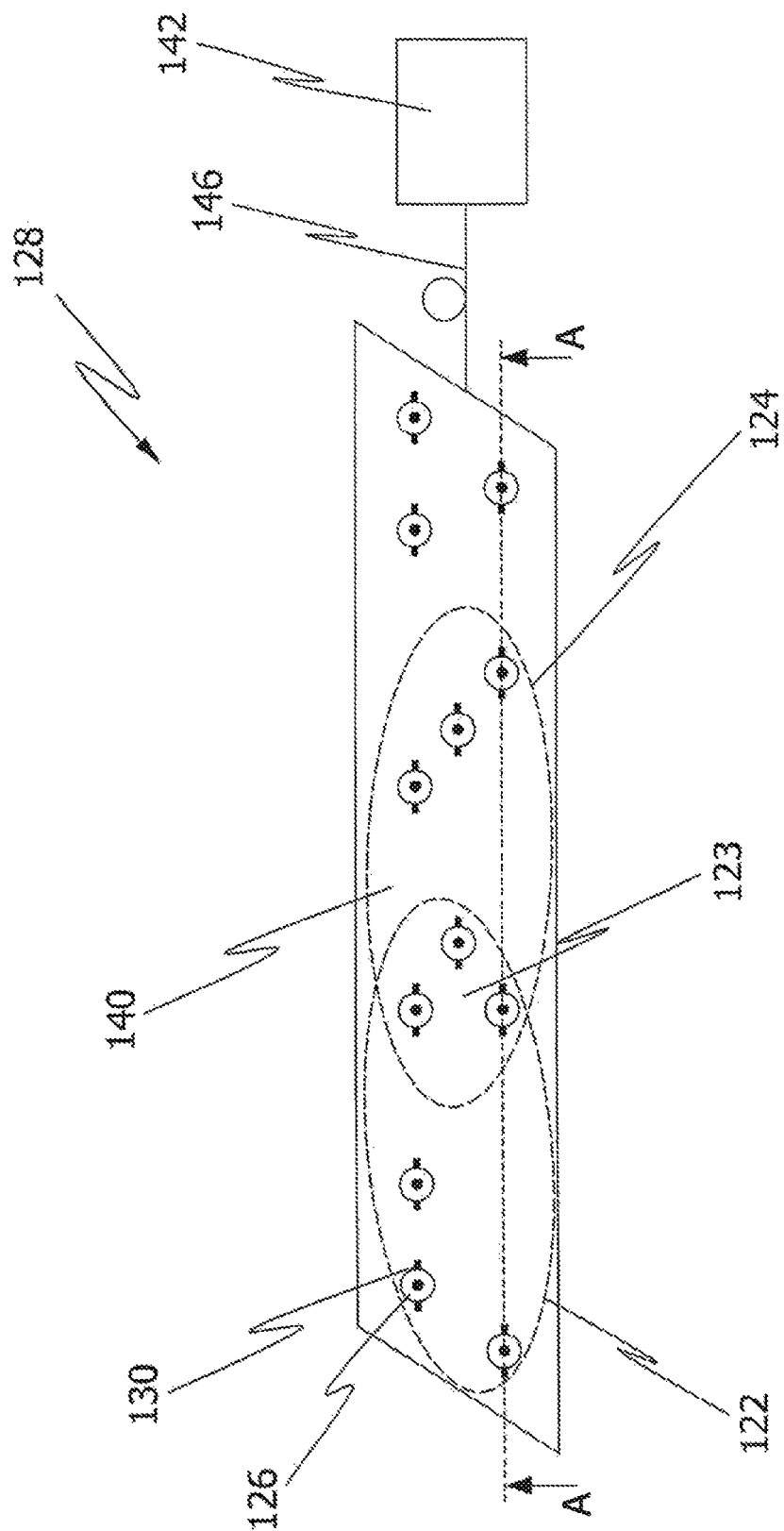
FIGS. 10 to 12 schematically illustrate further embodiments of the registration device shown in FIGS. 8 and 9.
Figure 11:
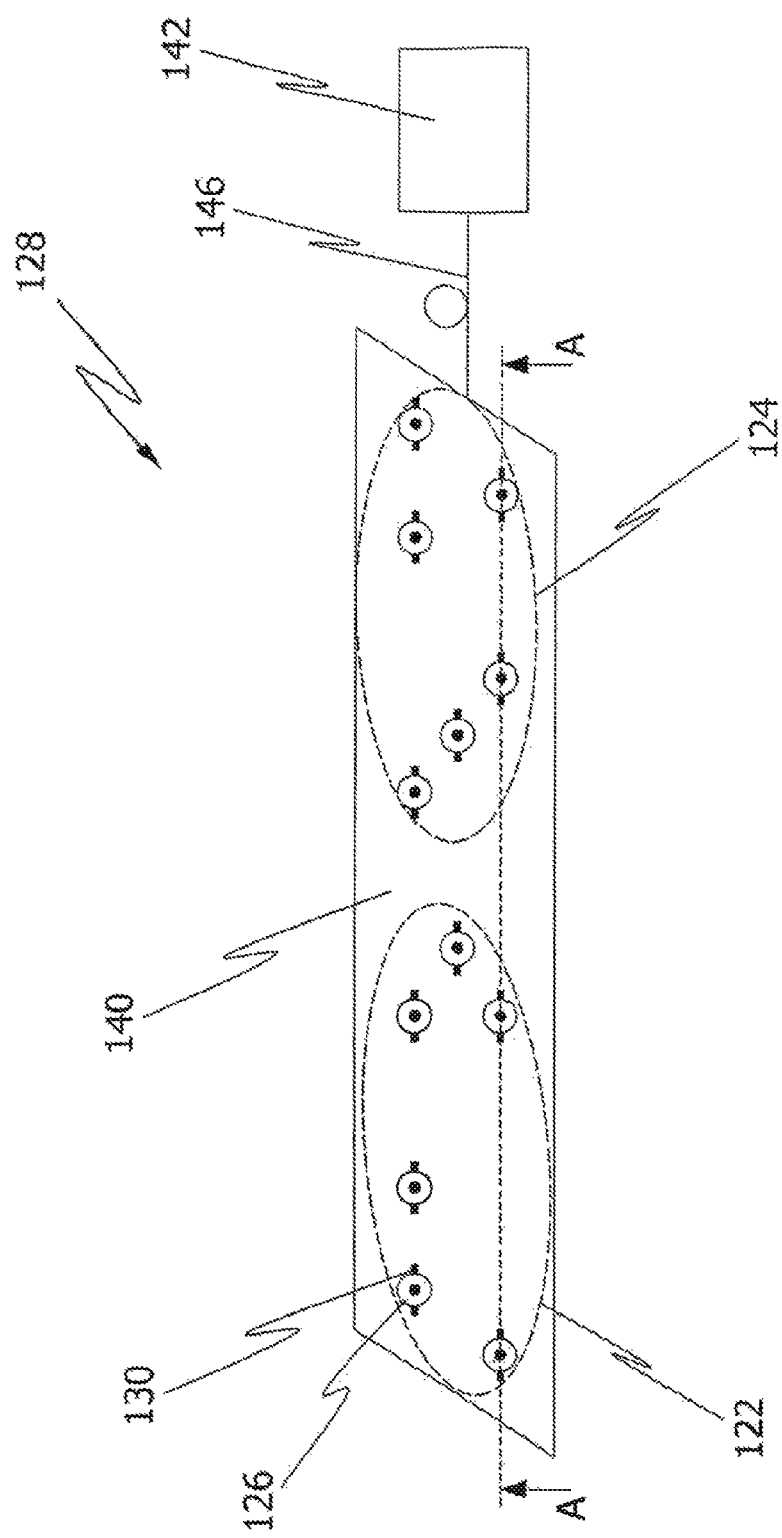
Figure 12:
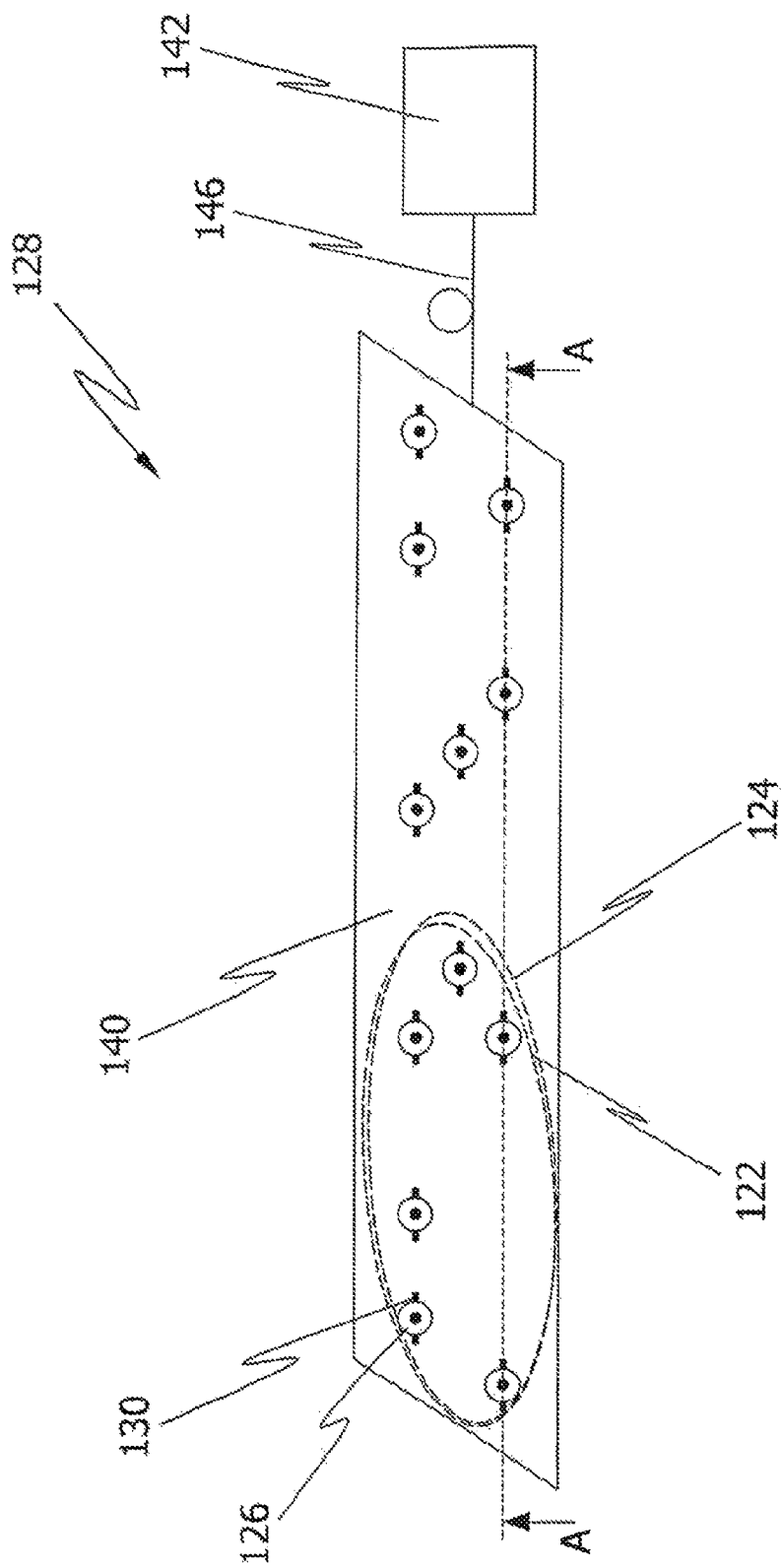

In the following, further embodiments of the registration device 128 illustrated in FIGS. 8 and 9 will be described in more detail. Referring to FIGS. 10 to 12, the registration device 128, in form of the flexible sheet 128, has portions 122 and 124 with emitters 126. These portions define the region 122 of the registration tracker 122 and the region 124 of the object tracker 124 on the sheet 128. Further, these regions may overlap each other.

FIG. 10 shows a registration device 128 similar to the registration device of the embodiment illustrated in FIGS. 8 and 9. As shown in FIG. 10, the registration tracker 122 defined by region 122 and the object tracker 124 defined by region 124 overlap at a region 123 having at least one common emitter 126. In the present case as shown in FIG. 10, the registration tracker 122 and the object tracker 124 have three common emitters 126 within the overlap region 123.

FIG. 11 illustrates another embodiment of the registration device 128, wherein the region 122 of the registration tracker 122 and the region 124 of the object tracker 124 are separated from each other. Thus, the registration tracker 122 and the object tracker 124 do not have common emitters 126.

FIG. 12 shows a further embodiment of the registration device 128. The region 122 of the registration tracker 122 and the region 124 of the object tracker 124 substantially define the same area on the sheet 128. In this case, the emitters 126 of the registration tracker 122 and of the object tracker 124 are identical. Thus, the registration tracker 122 and the object tracker 124 may form one tracker.

As has become apparent from the above description of preferred embodiments, the registration technique presented herein comprises various aspects, such as methods, systems, devices and device kits. Each individual aspect facilitates registration procedures when an imaging procedure during an ongoing navigation process is needed. For example, certain embodiments of the registration technique do not require the attachment of trackers to imaging devices nor the attachment of reference markings to an object of interest.

It is believed that many advantages of the present invention will be fully understood from the forgoing description, and it will be apparent that various changes may be made in the form, construction and arrangement of the exemplary aspects thereof without departing from the scope of the invention or without sacrificing all of its advantages. Because the invention can be varied in many ways, it will be recognized that the invention should be limited only by the scope of the following claims.

The invention claimed is:

1. A method of registering image data of an object with at least one of a location and an orientation of the object, the method comprising:
providing three-dimensional image data generated for the object, the image data being representative of at least a portion of the object and of reference markings associated with the object, wherein the reference markings have a known spatial relationship with a registration tracker adapted to be tracked by a navigation system;
providing registration tracking data representative of at least one of a spatial location and a spatial orientation of the registration tracker;
providing object tracking data representative of at least one of a spatial location and a spatial orientation of an object tracker adapted to be tracked by the navigation system, wherein the object tracker has a fixed spatial relationship with the object;
calculating from the registration tracking data and the object tracking data for a given point in time the relative position between the registration tracker and the object tracker; and
generating registered image data representative of at least one of the location and the orientation of the object taking into account the spatial relationship between the reference markings and the registration tracker and the relative position between the registration tracker and the object tracker.

2. The method of claim 1, wherein generating the registered image data comprises:
determining at least one of the position and orientation of the object tracker and of the registration tracker from the object tracking data and the registration tracking data, respectively, in relation to a first coordinate system associated with the navigation system;
automatically determining the reference markings in the image data in relation to a second coordinate system associated with the three-dimensional image data; and
performing a coordinate transfer of the coordinates of the object tracker from the first coordinate system into the second coordinate system via the registration tracker and the reference markings.

3. The method of claim 1, wherein the registration tracker has at least one of a loose and arbitrary spatial relationship with the object and/or an arbitrary spatial relationship with the object tracker.

4. The method of claim 1, wherein respective object tracking data for two or more object trackers are provided, with each object tracker having a fixed spatial relationship with different objects or different parts of the object.

5. The method of claim 1, further comprising providing a registration device comprising the reference markings and the registration tracker, wherein the registration device defines the known spatial relationship between the reference markings and the registration tracker.

6. The method of claim 5, wherein the registration device is at least one of loosely and arbitrarily co-located with the object such that at least the reference markings are placed in an image volume of an imaging device upon generation of the image data by the imaging device.

7. The method of claim 5, further comprising positioning the registration device independently from the object tracker prior to generation of the image data.

8. The method of claim 5, wherein the registration device further comprises the object tracker, wherein the registration device defines the spatial relationship between the object tracker and the object.

9. The method of claim 5, wherein the registration device comprises an adhesive layer to attach the registration device to the object, such that at least the reference markings are placed in an image volume of an imaging device upon generation of the image data by the imaging device.

10. The method of claim 1, further comprising at least one of stopping the provision of the registration tracking data and removing at least one of the registration tracker and the reference markings after generation of the registered image data.

11. The method of claim 1, further comprising continuing the provision of the object tracking data after generation of the registered image data.

12. The method of claim 11, further comprising displaying image data representative of at least one of the current location and the current orientation of the object taking into account the current object tracking data.

13. The method of claim 1, wherein the given point in time coincides with or lies shortly before or after generation of the image data.

14. The method of claim 1, wherein the object is at least one of a body part, an implant and a surgical instrument.

15. A computer program product comprising program code portions stored on a non-transitory computer-readable medium for performing the steps of any of the preceding claims when the computer program product is run on a computing device.

16. A device kit for assisting the registration of image data of an object with at least one of a location and an orientation of the object, the kit comprising:
a registration device comprising reference markings for an imaging device and a registration tracker configured to be tracked by a navigation system, wherein the registration device defines a known spatial relationship between the reference markings and the registration tracker and wherein the registration device is configured to assume a stable position when associated with the object; and an object tracker configured to be tracked by the navigation system, wherein the object tracker has an attachment mechanism to be firmly attached to the object in a fixed spatial relationship with the object.

17. The device kit of claim 16, wherein the registration device has an essentially linear form and is configured to receive the reference markings and the registration tracker at opposite ends thereof.

18. The device kit of claim 16, wherein the registration device is configured to be loosely associated with the object.

19. The device kit of claim 16, wherein the registration device has three or more fingers or tabs extending in different directions, wherein each finger or tab constitutes or carries at least one of the reference markings.

20. The device kit of claim 16, wherein the registration device is configured to be mounted on the object and comprises a flexible substrate and an adhesive layer to attach the substrate to the object.

21. The device kit of claim 20, wherein the registration device comprises emitters which are attached to the flexible substrate at connection points, wherein the emitters or the connection points function as the reference markings for the imaging device.

22. The device kit of claim 21, wherein the registration device comprises at least three emitters at predetermined locations, wherein each emitter is in a fixed relation to its neighbouring emitter.

23. A system for registering image data of an object with at least one of a location and an orientation of the object, the system comprising:
  an interface configured to receive three-dimensional image data generated for the object, the image data being representative of at least a portion of the object and of reference markings associated with the object, wherein the reference markings have a known spatial relationship with a registration tracker for tracking by a navigation system;
  a processor providing registration tracking data representative of at least one of a spatial location and a spatial orientation of the registration tracker and object tracking data representative of at least one of a spatial location and a spatial orientation of an object tracker for tracking by the navigation system, wherein the object tracker has a fixed spatial relationship with the object;
  wherein the processor calculates from the registration tracking data and the object tracking data for a given point in time the relative position between the registration tracker and the object tracker and generates registered image data representative of at least one of the location and the orientation of the object taking into account the spatial relationship between the reference markings and the registration tracker and the relative position between the registration tracker and the object tracker.

24. The system of claim 23, further comprising the device kit of claim 16.

25. The system of claim 23, further comprising a registration device including the reference markings for an imaging device and the registration tracker, wherein the registration device defines a known spatial relationship between the reference markings and the registration tracker, and wherein the registration device includes the object tracker.

26. The system of claim 25, wherein the registration device is configured to be mounted on the object and comprises a flexible substrate and an adhesive layer to attach the substrate to the object.

27. The system of claim 26, wherein the registration device comprises emitters which are attached to the flexible substrate at connection points, wherein the emitters or the connection points function as the reference markings for the imaging device.

28. A registration device for assisting the registration of image data of an object with at least one of a location and an orientation of the object, the registration device comprising:
  reference markings for an imaging device and a registration tracker for tracking by a navigation system, wherein the registration device defines a known spatial relationship between the reference markings and the registration tracker;
  an object tracker configured to be tracked by the navigation system; and
  a flexible substrate configured to be attached to the object, wherein the registration tracker and the object tracker comprise at least three emitters attached to the substrate at predetermined locations.

29. The registration device of claim 28, wherein the registration tracker is operative during registration and the object tracker is operative after registration, wherein the emitters of the registration tracker and of the object tracker are configured to be illuminated independently.

* * * * *